(12) United States Patent
Van De Sluis et al.

(10) Patent No.: US 11,270,793 B2
(45) Date of Patent: Mar. 8, 2022

(54) METHOD AND SYSTEM FOR DETERMINING PATIENT STATUS

(71) Applicant: KONINKLIJKE PHILIPS N.V., Eindhoven (NL)

(72) Inventors: Bartel Marinus Van De Sluis, Eindhoven (NL); Roel Peter Geert Cuppen, Venlo (NL)

(73) Assignee: KONINKLIIKE PHILIPS N.V., Eindhoven (NL)

( * ) Notice: Subject to any disclaimer, the term of this patent is extended or adjusted under 35 U.S.C. 154(b) by 750 days.

(21) Appl. No.: 14/427,405

(22) PCT Filed: Sep. 5, 2013

(86) PCT No.: PCT/IB2013/058301
§ 371 (c)(1),
(2) Date: Mar. 11, 2015

(87) PCT Pub. No.: WO2014/049474
PCT Pub. Date: Apr. 3, 2014

(65) Prior Publication Data
US 2015/0213205 A1    Jul. 30, 2015

Related U.S. Application Data

(60) Provisional application No. 61/706,239, filed on Sep. 27, 2012.

(51) Int. Cl.
*A61B 5/00* (2006.01)
*G16H 40/67* (2018.01)
*G16H 40/20* (2018.01)
(Continued)

(52) U.S. Cl.
CPC .............. *G16H 40/67* (2018.01); *A61B 5/002* (2013.01); *A61B 5/1113* (2013.01);
(Continued)

(58) Field of Classification Search
CPC ....... A61B 5/002; A61B 5/1118; A61B 5/165; A61B 5/4809; A61B 5/6889; A61B 5/7445; A61B 5/746; G06Q 10/0633
(Continued)

(56) References Cited

U.S. PATENT DOCUMENTS

| 2004/0032426 A1* | 2/2004 | Rutledge | G06F 19/322 715/764 |
| 2007/0132597 A1* | 6/2007 | Rodgers | A61B 5/1113 340/573.1 |
| 2008/0055074 A1 | 3/2008 | Gao et al. | |
| 2009/0054735 A1 | 2/2009 | Higgins et al. | |
| 2009/0216556 A1* | 8/2009 | Martin | G06Q 50/24 705/3 |

(Continued)

FOREIGN PATENT DOCUMENTS

CN           101095629 A      1/2008

OTHER PUBLICATIONS

Watch Report review of the Abacus Wrist PDA (published Feb. 14, 2005, available at https://www.watchreport.com/review-of-the-abacus-wrist-pda-au5005).*

*Primary Examiner* — Mark Holcomb (57) ABSTRACT

A system, method and tangible computer readable storage medium for receiving, from each of a plurality of sensors disposed in one of a plurality of patient rooms in a hospital ward, data relating to a corresponding patient housed in the one of the plurality of patient rooms, receiving data relating to an output destination, generating a prioritized list including one or more of the plurality of the patients based on the data relating to the plurality of patients and the data relating to the output destination and sending the list to the output destination.

20 Claims, 3 Drawing Sheets

(51) Int. Cl.
  *A61B 5/11*     (2006.01)
  *A61B 5/16*     (2006.01)
  *G06Q 10/06*    (2012.01)

(52) U.S. Cl.
  CPC ........... *A61B 5/1118* (2013.01); *A61B 5/165* (2013.01); *A61B 5/4809* (2013.01); *A61B 5/6889* (2013.01); *A61B 5/746* (2013.01); *A61B 5/7445* (2013.01); *G06Q 10/0633* (2013.01); *G16H 40/20* (2018.01)

(58) Field of Classification Search
  USPC ........................................................ 705/2–4
  See application file for complete search history.

(56) References Cited

U.S. PATENT DOCUMENTS

| | | | |
|---|---|---|---|
| 2009/0313046 A1* | 12/2009 | Badgett | G06F 19/327 |
| | | | 705/3 |
| 2010/0205003 A1 | 8/2010 | Brown | |
| 2010/0217618 A1* | 8/2010 | Piccirillo | G06Q 10/06375 |
| | | | 705/2 |
| 2010/0305966 A1* | 12/2010 | Coulter | G06Q 10/04 |
| | | | 705/2 |
| 2011/0087756 A1* | 4/2011 | Biondi | G06F 19/3418 |
| | | | 709/217 |
| 2011/0106565 A1* | 5/2011 | Compton | G06Q 50/22 |
| | | | 705/3 |
| 2011/0153341 A1* | 6/2011 | Diaz-Cortes | G16H 10/60 |
| | | | 705/2 |
| 2012/0203564 A1 | 8/2012 | Myr | |
| 2013/0300573 A1 | 11/2013 | Brown et al. | |

* cited by examiner

METHOD AND SYSTEM FOR DETERMINING PATIENT STATUS

CROSS-REFERENCE TO PRIOR APPLICATIONS

This application is the U.S. National Phase application under 35 U.S.C. § 371 of International Application No. PCT/IB2013/058301, filed on Sep. 3, 2013, which claims the benefit of U.S. Provisional Application No. 61/706,239, filed on Sep. 27, 2012. These applications are hereby incorporated by reference herein.

In hospital wards, staff typically treat large numbers of patients having a variety of conditions and at differing points in the course in the course of their treatment. Therefore, hospital staff should be informed about the status of the variety of patients being treated in order to optimize their work flow, prioritize the order in which patients are visited, and react to sudden changes in patient status in a timely manner. Advances in sensing technology have enabled, and will continue to enable, a variety of ways to sense patient status using sensors in and around a hospital bed. These sensors are becoming more affordable, and may become part of virtually every patient room in hospitals in the future. Therefore, the information collected by such sensors should be routed to hospital staff in order to enable them to use the information to optimize patient care.

A method for receiving, from each of a plurality of sensors disposed in one of a plurality of patient rooms in a hospital ward, data relating to a corresponding patient housed in the one of the plurality of patient rooms, receiving data relating to an output destination, generating a prioritized list including one or more of the plurality of the patients based on the data relating to the plurality of patients and the data relating to the output destination and sending the list to the output destination.

A system having a plurality of patient sensor networks, each of the patient sensor networks comprising one or more sensors, each of the patient sensor networks monitoring a corresponding one of a plurality of patients and being disposed in a corresponding patient room in a hospital ward and a priority management system receiving patient data from the plurality of patient sensor networks, the priority management system further receiving recipient parameters relating to a recipient of a prioritized list, the priority management system further generating the prioritized list based on the patient data and the recipient parameters.

A tangible computer-readable storage medium storing a set of instructions executable by a processor. The execution of instructions causing the processor to perform a method for receiving, from each of a plurality of sensors disposed in one of a plurality of patient rooms in a hospital ward, data relating to a corresponding one of a plurality of patients housed in one of the plurality of patient rooms, receiving data relating to an output destination, generating a prioritized list including one or more of the plurality of the patients based on the data relating to the plurality of patients and the data relating to the output destination.

The exemplary embodiments may be further understood with reference to the following description of exemplary embodiments and the related appended drawings, wherein like elements are provided with the same reference numerals. Specifically, the exemplary embodiments relate to methods and systems for determining patient status information and providing the patient status information to interested parties.

Hospital staff working in a hospital ward typically treat large numbers of patients having a variety of conditions and at differing points in the course in the course of their treatment. To optimize their work flow, hospital staff should be informed about the status of the variety of patients being treated. This may enable them to prioritize the order in which patients are visited and react to sudden changes in patient status in a timely manner. Advances in sensing technology have enabled, and will continue to enable, a variety of ways to sense patient status using sensors in and around a hospital bed. These sensors are becoming more affordable, and may become part of virtually every patient room in hospitals in the future. Therefore, the information collected by such sensors should be routed to hospital staff in order to enable them to use the information to optimize patient care. The exemplary embodiments provide a system and method for collecting data from these types of sensors, processing the data, and providing it to hospital staff such as nurses in a manner that enables them to optimize the performance of their work.

Figure 1:
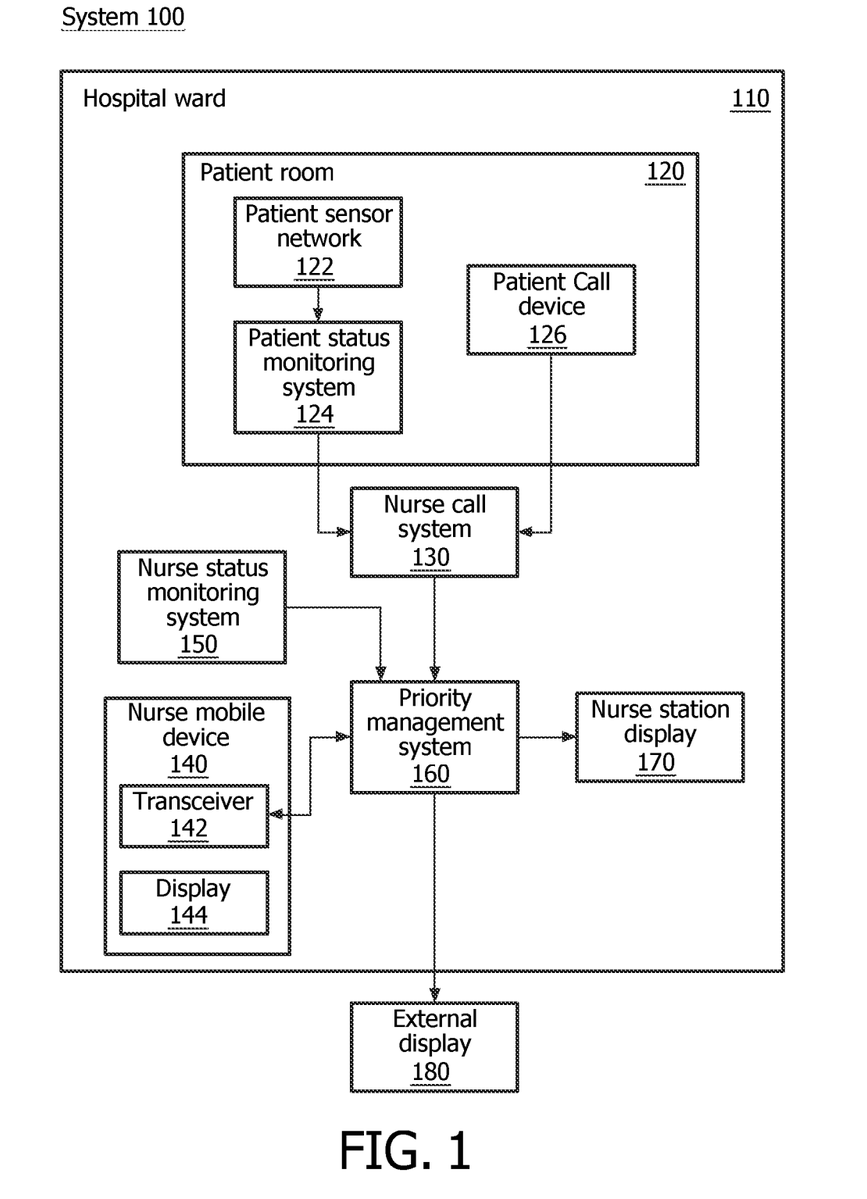
FIG. 1 illustrates an exemplary method for determining patient status and providing patient status information to interested parties.

FIG. 1 illustrates an exemplary system 100 for determining patient status information and providing the patient status information to interested parties. Those of skill in the art will understand that the specific elements of the system 100 described hereinafter are only exemplary, and that the broader principles described in the present application should not be understood to be limited to embodiments with these specific elements. The arrows connecting the elements shown in FIG. 1 represent the flow of information between the various elements. The system 100 is implemented in a hospital ward 110, represented schematically therein.

The hospital ward 110 includes a patient room 120. Those of skill in the art will understand that an actual hospital ward will include a plurality of rooms, and that the specific number of rooms will vary among differing hospitals and among differing wards within a given hospital. FIG. 1 is limited to a hospital ward 110 with a single patient room 120 for purposes of clarity of illustration.

The patient room 120 includes a patient sensor network 122. The patient sensor network 122 may include a plurality of sensors including, but not limited to, sensors disposed on the body of the patient, sensors disposed on or in the hospital bed, environmental sensors, etc. It will be apparent to those of skill in the art that the specific nature of the sensors included in the patient sensor network 122 may vary among differing embodiments, and that the types of sensors described above, and the data collected by the sensors that will be described below, are only exemplary. It will be further apparent to those of skill in the art that a patient room 120 may house, for example, two patients rather than a single patient, and that a patient room 120 housing more than one patient will include a separate patient sensor network 122 for each patient housed therein. It will be further apparent to those of skill in the art that, in other embodiments, a single integrated patient sensor network 122 may span multiple patient rooms, or that, in still other embodiments, a patient sensor network 122 may be a mobile apparatus that is disposed on the patient's body (e.g., worn or carried).

The patient sensor network 122 collects a variety of types of data about the patient being monitored thereby. Those of skill in the art will understand that different types of data may be prioritized and weighted by their priority as will be described hereinafter. The types of data to be collected by the patient sensor network 122 herein will be described in one possible order of priority, though those of skill in the art will understand that the specific priority order described herein is only exemplary, and that other orders of prioritization are possible. A first type of data that may be collected by patient sensor network 122 is patient vital signs. This may include patient heart rate, patient respiration rate, patient body temperature, patient blood pressure, and patient skin color. Patient vital signs are typically measured using sensors disposed on the body of the patient and known in the art, though those of skill in the art will understand that other types of sensors may alternately be used, such as more compact or wireless sensors that allow the patient to move around the patient room 120 without inconvenience.

A second type of data that may be collected by patient sensor network 122 is measurements indicative of pain, stress, or other emotions. In one exemplary embodiment, pain level and stress level is determined based on patient skin conductivity (e.g., if the patient's skin conductivity is higher, this indicates that the patient is sweating, which in turn indicates discomfort or stress being experienced by the patient), which may be measured by a sensor disposed on the body of the patient. In another embodiment, the patient may indicate pain or stress level subjectively. Data relating to patient pain or stress may also be collected based on heart rate variability or blood pressure. Additionally, patient stress level may be determined based on monitoring of patient facial expression, such as by using a camera disposed within patient room 120 to capture images of the patient and facial analysis software to determine whether the patient's facial expression indicates that the patient is experiencing pain.

A third type of data that may be collected by patient sensor network 122 is data relating to the patient's sleep status. Data relating to patient sleep status includes the amount and quality of recent sleep. The data may also include the patient's current sleep stage (e.g., awake, falling asleep, light sleep, deep sleep, etc.), and for how long the patient has been in the current stage (e.g., awake for three hours). Data about the patient's sleep status may be determined using, for example, a combination of data from sensors on the patient (e.g., a slow and steady respiratory rate may indicate restful sleep) and sensors in the bed (e.g., if the patient is moving within the bed, it may indicate that the patient is awake).

A fourth type of data that may be collected by patient sensor network 122 is data relating to the patient's activities. Patient activity data may include the general activity level of the patient, whether the patient is in and out of bed, whether and how often the patient has used the shower, and whether the patient has left the room. Patient activity data may be measured using a combination of sensors (e.g., accelerometers) on the body of the patient, sensors in the hospital bed, and environmental sensors. In one exemplary embodiment, an activity monitor may be carried in a manner so as to keep the sensor at a constant body position (e.g., around the patient's neck or in the patient's pocket) in order to improve the reliability of the measured data.

A fifth type of data that may be collected by patient sensor network 122 is data relating to the patient's social status. Patient social status data may include whether the patient is alone, is talking with a doctor, is receiving visitors, is using the restroom, is being washed and/or dressed, etc. Patient social status data may be measured using a combination of sensors on the body of the patient, sensors in the hospital bed, and environmental sensors.

As noted above, those of skill in the art will understand that the order of prioritization discussed above is only exemplary, and that other orders of prioritization are possible. In another embodiment, the order of prioritization may be modifiable by a medical professional (e.g., a doctor or a nurse). In such an embodiment, the order may be modifiable on a per-patient basis. Alternately, the order may be modifiable on a per-type-of-patient basis; for example, for an orthopedic patient or a patient with mental health issues, sleep status may be more important than vital signs.

Additionally, while the above-described data measurements relate specifically to measurement by sensors, those of skill in the art will understand that other types of data collection are possible without departing from the broader principles of the exemplary embodiments. For example, data about pain, sleep, stress, etc., could be collected from a database storing the results of questionnaires given to patients or ratings made by staff members. In one example, data used may be from activities of daily life ("ADL") ratings.

Data from the patient sensor network 122 is received by a patient status monitoring system 124. Though the system 100 shown in FIG. 1 includes a patient status monitoring system 124 disposed in the patient room 120, those of skill in the art will understand that, in other embodiments, the patient status monitoring system may be located elsewhere. For example, in one alternative embodiment, the patient status monitoring system 124 may be implemented as a software module executed by a centrally located system to monitor each of the patients in the hospital. The patient status monitoring system 124 monitors the data for the patient being monitored by patient sensor network 122 and uses the information to determine whether a call to a nurse, or other health care professional, is necessary, and generates such a call if necessary.

In addition to the patient sensor network 122, input may be collected from a patient call device 126, which enables the patient to request a visit from a nurse or other health care professional. In some embodiments, the patient call device 126 may be a simple call button enabling the patient to request a visit, while in other embodiments, the patient may be provided with a panel of buttons enabling the patient to make different kinds of calls (e.g., request a nurse, request food or drink, indicate an emergency, etc.).

The system 100 also includes a nurse call system 130, which receives patient-generated nurse calls from the patient call device 126 and system-generated nurse calls from the patient status monitoring system 124. The nurse call system 130 also receives patient status information that has been recorded by the patient sensor network 122, via the patient status monitoring system. All calls and measured data are then sent by the nurse call system 130 to a priority management system 160, which will be discussed in further detail hereinafter. In some embodiments, the nurse call system 130 may be an integrated element of the priority management system 160. In other embodiments, such as the embodiment illustrated in FIG. 1, the nurse call system 130 and the priority management system 160 may be separate elements adapted to communicate with one another; this may be appropriate, for example, where the hospital ward 110 has an existing nurse call system 130 prior to the implementation of the priority management system 160.

The system 100 also includes a nurse mobile device 140. The nurse mobile device 140 may be carried by a nurse working in hospital ward 110. Those of skill in the art will understand that, though FIG. 1 illustrates a single nurse mobile device 140, there may be multiple nurses working in a typical hospital ward 110, and each of them may carry a nurse mobile device 140. The nurse mobile device 140 is a mobile computing device, which may be a dedicated combination of hardware and software for hospital use, or may be a general-purpose mobile computing device (e.g., a smart phone) executing software for performing the functions described herein. The nurse mobile device 140 includes, among other components, a transceiver 142 and a display 144; those of skill in the art will understand that this is not an exhaustive list of the elements of the nurse mobile device 140. In one exemplary embodiment, the nurse mobile device 140 may be a device that is worn, rather than carried, such as a device that is worn on the wrist, augmented reality glasses projecting information into the wearer's field of vision, or a headset providing audible alerts or spoken information (e.g., generated using speech synthesis). In another exemplary embodiment, the nurse mobile device 140 may include a location sensing element (e.g., a GPS receiver) that may enable determination of the position of the nurse carrying nurse mobile device 140, in conjunction with the nurse status monitoring system 150 which will be described below.

The transceiver 142 may be any type of transceiver that allows the nurse mobile device 140 to communicate with the priority management system 160, which will be described in further detail hereinafter; this may include a personal-area network transceiver, a local-area network transceiver, a wide-area network transceiver, a cellular transceiver, another type of transceiver not described herein, or combinations of multiple types of transceivers.

The system 100 also includes nurse status monitoring system 150. The nurse status monitoring system 150 monitors the location and activity of nurses within the hospital ward 110. This may be accomplished using, for example, global positioning system receivers, or a dedicated indoor positioning system based on, e.g., a received signal strength ("RSS") location algorithm, image processing techniques applied to recorded video, or combinations of multiple types of position sensing elements. In one exemplary embodiment, the nurse status monitoring system 150 may communicate with an element of the nurse mobile devices 140 to determine the position and/or activity level of the nurses within the hospital ward 110.

The system 100 also includes priority management system 160, which, as described above, receives patient data sensed by patient sensor network 122, patient-generated nurse calls from patient call device 126, and system-generated nurse calls from the patient status monitoring system 124. The priority management system 160 also receives, from the nurse status monitoring system 150, locations and activity levels of nurses within the hospital ward 110. Based on the various received data, the priority management system 160 generates one or more prioritized lists of patients.

Each list may be separately generated based on where it will be displayed, the recipient of the list, the patient data, etc. For example, a list to be displayed on a nurse mobile device 140 may be limited to include a subset of patients who are the responsibility of the nurse carrying the nurse mobile device 140, or in the vicinity of the current location of the nurse. A list to be displayed at a nurse station or other central location may include all patients in the hospital ward 110, or, alternately, all patients in the hospital ward 110 who should be visited by a nurse (based on a manual nurse call, an automatically generated nurse call, etc.). A list to be shown on a display located outside patient room 120 may include only the patients located in the patient room 120, only patients located in the patient room 120 who have made a nurse call, only patients located in the patient room 120 who are awake, etc. Additionally, the list may be sorted based on the priority of the patients included in the list. For example, patients having critical changes in their status (e.g., patients who have experienced critical changes in their vital signs) may be presented before other patients. In other words, the contents and prioritization of the list are determined not solely based on the patient data, but also based on the intended destination of the output of the priority management system 160.

Additionally, the prioritized lists generated by the priority management system 160 may contain additional patient data beyond a simple ordered list of names. For example, important vital signs may be shown for all patients on one such list, or for all patients having critical changes in their status. The display of vital signs may be static, or may switch between different types of patient status, such as vital signs, clinical healing status as determined by hospital staff, social status, current activity, etc. Patients having critical changes in their status may be displayed more prominently (e.g., in larger text, a differing color, or in any other manner known in the art). In another embodiment, the list may be accompanied by a visual snapshot of the patient.

As noted above, a prioritized list may be provided to nurse mobile device 140 for display on display 144. The contents and prioritization of such a list may be determined based on the nurse's role in the hospital ward 110, the nurse's level of experience and/or area of expertise, the activity level of the nurse (e.g., whether the nurse is presently busy or unoccupied), the location of the nurse mobile device, the status of the various patients within the hospital ward 110, etc.

The system 100 also includes a nurse station display 170 receiving, from the priority management system 160, one such prioritized list as described above. The nurse station display 170 may be located at a nurse station or other central location within hospital ward 110. The prioritized list provided thereto may include all patients within the hospital ward 110, or a subset selected based on factors such as the existence of patient calls, changes in vital signs, etc. In one embodiment, the prioritized list shown at nurse station display 170 may alternate between a display of all patients within the hospital ward 110 and a display of only patients requiring immediate attention. In another embodiment, the nurse station display 170 may include a graphical user interface allowing a nurse or other user to select one patient and receive further information (e.g., a full display of all sensed patient data) about the selected patient. However, as described herein, the specific nature of the list provided to nurse station display 170 may vary among differing embodiments, based on priorities determined by the hospital or the nurses working in the hospital ward 110, or based on various other factors that may be apparent to those of skill in the art.

The system 100 also includes an external display 180. Unlike the nurse station display 170, the external display 180 is located outside the hospital ward 110. The external display 180 may receive a prioritized list from the priority management system, in the same manner as described above. The external display 180 may be stationary or mobile, and may be located at a point within the hospital but outside the hospital ward 110, or may be located outside the hospital. In one embodiment, the external display 180 may be at a location where it may be seen by hospital support staff (e.g., cleaning staff, catering staff), and may be used to direct support staff toward patients who are awake, or away from patients experiencing critical conditions. In another embodiment, the external display 180 may be provided on a mobile device (e.g., a smart phone) used by a doctor, and may provide data relating to patients being treated by the doctor. Those of skill in the art will understand that these are only examples, that other types of external displays 180 are possible, and that the specific contents and prioritization of a list provided to the external display may vary among differing embodiments.

Figure 2:
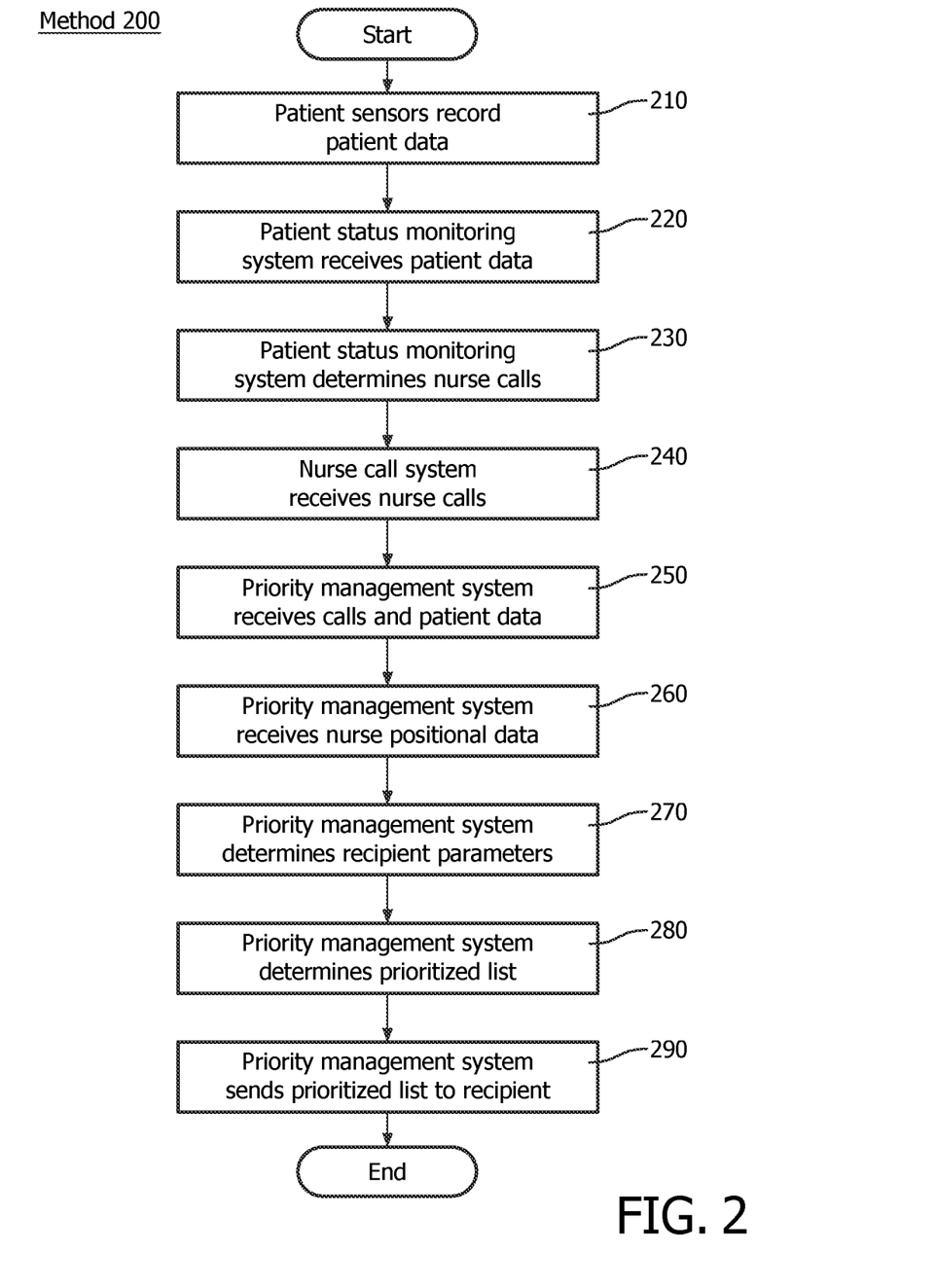
FIG. 2 illustrates an exemplary system for determining patient status and providing patient status information to interested parties according to a method such as the exemplary method of FIG. 1.

FIG. 2 illustrates an exemplary method 200 for determining patient status information and providing the patient status information to interested parties. Those of skill in the art will understand that, though the method 200 will be described with specific reference to the elements of the system 100 described above, this is only exemplary, and that the method 200 may be implemented by any other combination of system elements capable of functioning in the manner described.

In step 210, patient data is sensed, for all patients within hospital ward 110, by the patient sensor network 122 monitoring each of the patients. The sensed patient data may be any or all of the types described above with reference to the patient sensor network 122. In step 220, the patient status monitoring system 124 receives the sensed patient data from the patient sensor network 122. In step 230, the patient status monitoring system 124 determines whether any calls should be generated based on the sensed patient data; those of skill in the art will understand that a wide variety of types and priorities of calls may be generated based on the sensed patient data.

In step 240, the nurse call system 130 receives any nurse calls generated by the patient status monitoring system 124 in step 230, or received directly from patients using the patient call device 126, along with the patient data sensed in step 210. In step 250, the priority management system 160 receives nurse calls and patient data from the nurse call system 130. In step 260, the priority management system 160 receives nurse positional and activity data from the nurse status monitoring system 150.

In step 270, the priority management system 160 determines parameters relating to the recipient of the prioritized list to be output by the method 200. As discussed above, the list may be comprised and prioritized differently depending on its recipient; for example, a list to be provided to the nurse mobile device 140 may include patients who are close to the nurse, while a list to be displayed at nurse station display 170 may include all patients in hospital ward 110. The priority management system 160 may determine these parameters based on the prompting that initiated the performance of method 200. For example, if, as discussed above, the method 200 is being performed continuously to update a nurse station display 170, then the parameters may be appropriate for such updating, whereas if the method 200 is being performed in response to a critical change in patient vitals, the parameters may be those appropriate for any recipients who should be informed of such a change.

In step 280, the priority management system 160 generates and prioritizes a list, as described above. In step 290, the priority management system 160 outputs the list to the appropriate destination, e.g. display 144 of nurse mobile device 140, nurse station display 170, external display 180, a display outside patient room 120, or any other destination not explicitly described herein. Following step 280, the method 200 terminates.

Figure 3:
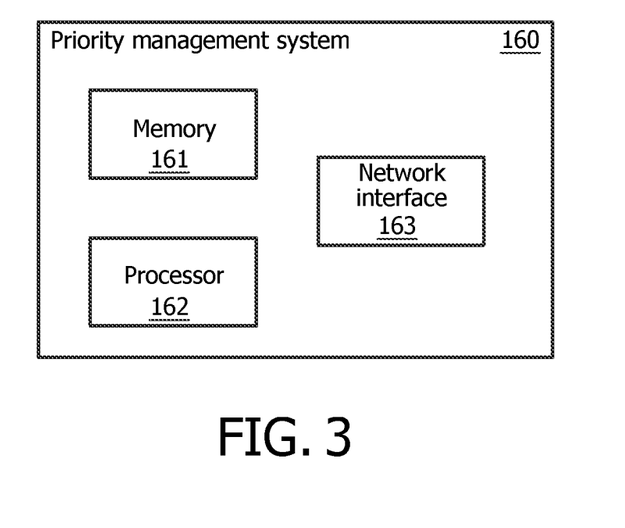
FIG. 3 illustrates a more detailed schematic view of the priority management system.

FIG. 3 illustrates a more detailed schematic view of the priority management system 160. Those of skill in the art will understand that the elements illustrated in FIG. 3 do not present an exhaustive list of all of the elements of priority management system 160, but, rather, that the priority management system 160 may include further elements not expressly mentioned herein. The priority management system 160 includes a memory 151 storing code that may be executed to perform tasks related to the performance of the method 200, such as the determination of the prioritized list in step 280, as well as a processor 152 executing such code. Those of skill in the art will understand that the memory 151 and processor 152 may be any hardware elements known in the art and capable of storing and executing computer-implemented instructions in the form of code. The priority management system 160 also includes a network interface 153 enabling communication with the other elements of the method 100; the network interface 153 may be any wired or wireless network interface, or combination of wired and wireless interfaces, known in the art for facilitating the transfer of data among differing computing elements. Those of skill in the art will understand that other elements of the system 100, such as the patient status monitoring system 124, the nurse call system 130, the nurse mobile device 140, the nurse station display 170, and the external display 180, may also include elements such as the memory, processor, and network interface described above.

It will be apparent to those of skill in the art that method 200 may be performed at various times and on various schedules. For example, in one embodiment, the method 200 may be performed continually to update a nurse station display on a real-time basis based on any change in patient status. In another embodiment, the method 200 may be performed each time a nurse call is generated by patient status monitoring system 124 or patient call device 126 indicating that a patient needs attention. In another embodiment, the method may be performed when initiated by a user, such as when a nurse using nurse mobile device 140 elects to refresh display 144, or when a member of hospital support staff begins using external display 180.

Therefore, the exemplary embodiments described above enable patient information to be determined and automatically provided to interested parties in a variety of manners. The patient information may be provided in the form of a prioritized list, which may be displayed on a variety of devices including both stationary and mobile devices. In one embodiment, the list can be prioritized by urgency based on the patient's status information. The list may be customized based on the viewer or viewers for which it is intended, may be individualized for an individual staff member to support the staff member's work flow, and may provide the viewers with information about various aspects of a patient's condition and treatment. The location of the staff member and the patients may be taken into account when generating the list. Additionally, medical professionals may be able to select a patient shown on the list and retrieve additional information about the selected patient. Further, a list that provides data about a patient urgently requiring care may be accompanied by an auditory alert to draw attention to the patient. Thus, the exemplary embodiments may provide information that may enable medical professionals to provide better care to patients.

Additionally, as discussed above, use of the exemplary embodiments is not limited to medical professionals; rather, the exemplary embodiments may be used by hospital support staff to guide their tasks as well. In one example, catering staff members who are serving breakfast can have their route planned starting at a side of a ward where patients are already awake, and service sleeping patients may be postponed. In another example, planning for a cleaner may take patient status into account, avoiding rooms where patients are sleeping, in severe stress or pain, or require privacy.

Those of skill in the art will understand that the above-described exemplary embodiments may be implemented in any number of matters, including as a software module, as a combination of hardware and software, etc. For example, the exemplary method 200 may be embodied in a program stored in a non-transitory storage medium and containing lines of code that, when compiled, may be executed by a processor.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made to the exemplary embodiments, without departing from the spirit or the scope of the invention. Thus, it is intended that the present invention cover modifications and variations of this invention provided they come within the scope of the appended claims and their equivalents.

What is claimed is:

1. A method for providing patient status information with a system, the system comprising one or more first sensors, one or more second sensors, and one or more processors, the method comprising:
   receiving, from the one or more first sensors, first sensor output signals indicating one or more physiological conditions of a plurality of patients in a hospital ward;
   receiving, from the one or more second sensors, second sensor output signals related to a present location and a present activity level of two or more nurses in the hospital ward;
   generating, with the one or more processors, at least: (a) a first prioritized list of the plurality of the patients for a first nurse of the one or more nurses; (b) a second prioritized list of the plurality of the patients for a second nurse of the one or more nurses; and (b) a third prioritized list of the plurality of the patients for a nurse station display,
   wherein the first prioritized list, the second prioritized list, and the third prioritized list are all different prioritized lists,
   wherein the first prioritized list includes a first subset of the plurality of the patients, and wherein the first subset of the plurality of the patients comprises more than one patient, the first prioritized list being generated based on (i) the first sensor output signals being indicative of a change in the one or more physiological conditions of the first subset of the plurality of the patients, (ii) the second sensor output signals being indicative of a present proximity of the first nurse to the first subset of the plurality of the patients and the present activity level of the first nurse in the hospital ward when the first prioritized list is generated, and (iii) a location where the first prioritized list will be displayed,
   wherein the second prioritized list includes a second subset of the plurality of the patients, and wherein the second subset of the plurality of the patients comprises more than one patient, the second prioritized list being generated based on (i) the first sensor output signals being indicative of a change in the one or more physiological conditions of the second subset of the plurality of the patients, (ii) the second sensor output signals being indicative of a present proximity of the first nurse to the second subset of the plurality of the patients and the present activity level of the second nurse in the hospital ward when the second prioritized list is generated, and (iii) a location where the second prioritized list will be displayed,
   wherein the third prioritized list includes each of the plurality of the patients;
   effectuating, with the one or more processors, presentation of the first prioritized list on a first client computer system associated with the first nurse, the second prioritized list on a second client computer system associated with the second nurse, and the third prioritized list on a nurse station display.

2. The method of claim 1, wherein the first sensor output signals indicate patient vital signs, patient stress, patient sleep status, patient activities, and patient social status.

3. The method of claim 2, wherein at least one of the first prioritized list, the second prioritized list, or the third prioritized list is augmented with a dynamic visualization of the first sensor output signals.

4. The method of claim 2, further comprising prioritizing, and weighting based on the priority, with the one or more processors, the patient vital signs, followed in priority order by the patient stress, the patient sleep status, the patient activities, and the patient's social status for individual patients when generating at least one of the first prioritized list, the second prioritized list, and the third prioritized list such that:
   a first patient whose vital signs indicate a change in the physiological conditions of the first patient is positioned ahead of a second patient whose stress, sleep status, activities, and/or social status indicate a change in the physiological conditions of the second patient in a prioritized list.

5. The method of claim 1, wherein the first client computer system associated with the first nurse comprises a wrist-worn device.

6. The method of claim 1, wherein the first prioritized list is further generated to one or more additional nurses based on one or more nurse calls.

7. The method of claim 6, wherein the nurse calls are generated based on patient vital signs.

8. The method of claim 1, further comprising:
   generating, with the one or more processors, an auditory alert if at least one of the first prioritized list, the second prioritized list, or the third prioritized list includes a patient requiring urgent care.

9. The method of claim 1, wherein the activity level of the first nurse in the hospital ward comprises presently (i) busy or (ii) unoccupied when the given prioritized list is generated.

10. The method of claim 1, wherein the method further comprises facilitating, with the one or more processors via the first client computer system associated with the first nurse, adjustment of the priority order by the first nurse.

11. The method of claim 1, further comprising generating a fourth prioritized list that is displayed on a fixed display outside a patient's room, the fixed display being separate from each of the nurse station display, the first client computer system associated with the first nurse and the second client computer system associated with the second nurse.

12. A system for providing patient status information, the system comprising:
one or more first sensors configured to generate first sensor output signals indicating one or more physiological conditions of a plurality of patients in a hospital ward;
one or more second sensors configured to generate second sensor output signals related to a present location and a present activity level of one or more nurses in the hospital ward; and
one or more processors configured by machine-readable instructions to:
receive, from the one or more first sensors, the first sensor output signals;
receive, from the one or more second sensors, the second sensor output signals;
generate at least: (a) a first prioritized list of the plurality of the patients for a first nurse of the one or more nurses; (b) a second prioritized list of the plurality of the patients for a second nurse of the one or more nurses; and (b) a third prioritized list of the plurality of the patients for a nurse station display, wherein the first prioritized list, the second prioritized list, and the third prioritized list are all different prioritized lists,
wherein the first prioritized list includes a first subset of the plurality of the patients, and wherein the first subset of the plurality of the patients comprises more than one patient, the first prioritized list being generated based on (i) the first sensor output signals being indicative of a change in the one or more physiological conditions of the first subset of the plurality of the patients, (ii) the second sensor output signals being indicative of a present proximity of the first nurse to the first subset of the plurality of the patients and the present activity level of the first nurse in the hospital ward when the first prioritized list is generated, and (iii) a location where the first prioritized list will be displayed;
wherein the second prioritized list includes a second subset of the plurality of the patients, and wherein the second subset of the plurality of the patients comprises more than one patient, the second prioritized list being generated based on (i) the first sensor output signals being indicative of a change in the one or more physiological conditions of the second subset of the plurality of the patients, (ii) the second sensor output signals being indicative of a present proximity of the first nurse to the second subset of the plurality of the patients and the present activity level of the second nurse in the hospital ward when the second prioritized list is generated, and (iii) a location where the second prioritized list will be displayed,
wherein the third prioritized list includes each of the plurality of the patients; and
effectuate presentation of the first prioritized list on a first client computer system associated with the first nurse, the second prioritized list on a second client computer system associated with the second nurse, and the third prioritized list on a nurse station display.

13. The system of claim 12, wherein the first sensor output signals indicate patient vital sign data, patient stress, data patient sleep status, patient activities, and patient social status.

14. The system of claim 13, wherein at least one of the first prioritized list, the second prioritized list, or the third prioritized list is augmented with a dynamic visualization of the first sensor output signals.

15. The system of claim 13, wherein the one or more processors are configured to prioritize, and weight based on the priority, the patient vital signs, followed in priority order by the patient stress, the patient sleep status, the patient activities, and the patient's social status for individual patients when generating at least one of the first prioritized list, the second prioritized list, and the third prioritized list such that:
a first patient whose vital signs indicate a change in the physiological conditions of the first patient is positioned ahead of a second patient whose stress, sleep status, activities, and/or social status indicate a change in the physiological conditions of the second patient in a prioritized list.

16. The system of claim 12, wherein the first client computer system associated with the first nurse comprises a wrist-worn device.

17. The system of claim 12, wherein the first prioritized list is further generated to one or more additional nurses based on one or more nurse calls, and wherein the nurse calls are generated based on patient vital signs.

18. The system of claim 12, wherein the activity level of the first nurse in the hospital ward comprises presently (i) busy or (ii) unoccupied when the given prioritized list is generated.

19. The system of claim 12, wherein the one or more processors are further configured to facilitate, via the first client computer system associated with the first nurse, adjustment of the priority order by the first nurse.

20. The system of claim 12, further comprising generating a fourth prioritized list that is displayed on a fixed display outside a patient's room, the fixed display being separate from each of the nurse station display, the first client computer system associated with the first nurse, and the second client computer system associated with the second nurse.

* * * * *